Figure 1:
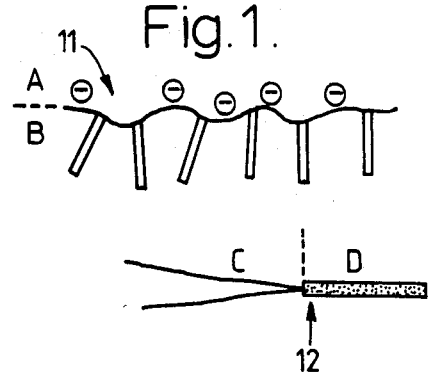

United States Patent [19]

Causton

[11] Patent Number: 4,663,202
[45] Date of Patent: May 5, 1987

[54] PREVENTION OF UNDESIRED ADSORPTION ON SURFACES

[75] Inventor: Brian E. Causton, North Waltham, England

[73] Assignee: National Research Development Corporation, London, England

[21] Appl. No.: 691,561
[22] PCT Filed: May 14, 1984
[86] PCT No.: PCT/GB84/00163
§ 371 Date: Jan. 14, 1985
§ 102(e) Date: Jan. 14, 1985
[87] PCT Pub. No.: WO84/04546
PCT Pub. Date: Nov. 22, 1984

[30] Foreign Application Priority Data

May 13, 1983 [GB] United Kingdom ................ 8313232

[51] Int. Cl.⁴ .......................... B05D 3/02; A61C 5/00
[52] U.S. Cl. .................................. 427/388.4; 106/35; 424/49; 427/388.5; 523/118; 524/765; 524/767
[58] Field of Search .................... 424/54, 49; 433/217; 427/388.4, 388.5; 524/765, 767; 523/118; 106/35

[56] References Cited

U.S. PATENT DOCUMENTS 4,082,884 4/1978 De Long .............................. 428/282
4,362,713 12/1982 Buck ..................................... 424/57

FOREIGN PATENT DOCUMENTS 0019602 11/1980 European Pat. Off. .
0057875 8/1982 European Pat. Off. .
0079406 5/1983 European Pat. Off. .
0105982 4/1984 European Pat. Off. .
0105983 4/1984 European Pat. Off. .
0105984 4/1984 European Pat. Off. .
0121656 10/1984 European Pat. Off. .
2307857 4/1976 France .
397123 2/1966 Switzerland .
1406884 9/1975 United Kingdom .
1497683 1/1978 United Kingdom .
2026004 1/1980 United Kingdom .
2027345 2/1980 United Kingdom .
2027045 2/1980 United Kingdom .
2034724 6/1980 United Kingdom .
2063892 6/1981 United Kingdom .
1603321 11/1981 United Kingdom .

OTHER PUBLICATIONS

McCutcheon's, Emulsifiers & Detergents, 1981, p. 235.
Kanebo, Chemical Abstracts, 86, 141765r, 1977.
Hitachi, Chemical Abstracts, 87, 24867k, 1977.
Chemical Abs., 1982, vol. 96:195112a.
Chemical Abs., 1976, vol. 84:166345a.
Chemical Abs., 1982, vol. 97:25240u.
R. S. Wilkinson, Proc. Annu. Mar. Coat. Conf., 1977, 17, IV-1-IV-9, "Anti-Fouling Self-Polishing, Co-polymers".
Mr. Fletcher and G. I. Loeb, Colloid and Interface Science, vol. III, pp. 459-469, Academic Press Inc., 1976-"The Influence of Substratum Surface Properties on the Attachment of a Marine Bacterium".
M. Kronstein, American Chemical Society-Div. Org. Coat. Plast. Chem. Paper, 1975, 35(2), pp. 64-71, "Symposium on New Concepts in Coatings and Plastics Chemistry: The Influence of Polymers on the Mechanism of Antifouling Paints".

Primary Examiner—Lorenzo B. Hayes
Attorney, Agent, or Firm—Oblon, Fisher, Spivak, McClelland & Maier

[57] ABSTRACT

A method of treating a surface to render the surface resistant to undesired adsorption from an aqueous environment, involving treating the surface with a solution containing a polymer mixture comprising (1) a polymer containing (a) reactive groups (A) capable of bonding with the surface to be treated and (b) hydrophobic groups (B); and (2) a polymer comprising (c) at least one hydrophilic polymeric chain (c) and (d) at least one hydrophobic group (D) in the presence of water. Compositions containing the polymer mixture may be used as mouthwashes to prevent or reduce tooth decay and prevent plaque formation. They may also be applied to various surfaces where prevention and/or reduction of colonization by microorganisms on the surfaces is desired.

28 Claims, 6 Drawing Figures

PREVENTION OF UNDESIRED ADSORPTION ON SURFACES

This invention relates to the prevention and/or reduction of undesired adsorbed build up on surfaces exposed to aqueous environments, especially such as leads to colonisation by micro-organisms.

There are many surfaces exposed to aqueous environments which are susceptible to undesired adsorbed build up of e.g. protein and/or mucopolysaccharide, which can for example result in colonisation by micro-organisms. The surfaces which suffer from this kind of build up are diverse in character. They include the surfaces of teeth where the bacteria which colonise the teeth cause tooth decay. The hulls of ships and marine structures submerged in water become fouled by micro-organisms which colonise them. The micro-organisms for example tend to slow the progress of ships. Cooling towers and heat exchangers become covered with slime which forms as a result of micro-organism build-up and their efficiency is reduced. In food processing plant equipment can become fouled for example by adsorption of protein from process liquid. These are some examples of some surfaces which suffer from fouling. However there are many other industrial and medical applications, which also suffer from undesired build-up, and domestic applications for example bacterial colonisation in lavatories.

Vast sums of money ar spent each year by industry in the cleaning of fouled surfaces and often industrial processes have to be stopped during the cleaning operation. Bactericides may be added to processing liquids to reduce the occurrence of fouling but the use of bactericides is restricted both from an environmental point of view and according to the particular equipment being treated. Indeed in some cases where for example cleaning is not practical fouled equipment has simply to be discarded. Attempts to treat surfaces to stop the build-up and retain efficiency have so far proved unsuccessful.

When a surface is exposed to an aqueous environment containing biotic material, there is first adsorbed onto the surface a layer of e.g. protein and/or muco-polysaccharide from the surrounding fluid. This layer forms very quickly. Its structure and composition varies according to the particular surface concerned and the composition of the fluid to which the surface is exposed but it is not yet fully understood. It is to this first adsorbed layer that the micro-organisms attach themselves. The form of bonding between the micro-organisms and the adsorbed layer is not yet fully understood and may vary according to the composition and structure of the adsorbed layer. If there is no first adsorbed layer the micro-organisms will not become bonded and accordingly the surfaces will not become colonised by the micro-organisms with the disadvantages relating thereto.

In addition adsorption of e.g. protein from an aqueous environment can itself be disadvantageous when it is on to apparatus walls for example during protein preparation. Here it can result in protein losses from the system thus decreasing its efficiency.

Attempts to provide surfaces, in particular those of teeth, protected from micro-organism build up using single polymer systems comprising monomers for bonding to the tooth surface and monomer non-adsorbing, e.g. to protein from the saliva, to prevent formation of the first adsorbed layer, have generally proved impractical. This is believed to be because the polymer tends to be deposited on the tooth surface in a more or less random fashion and it can take at least several days, if not more, before there is any orientation of the polymer on the tooth surface such that the bonding groups attach to the teeth surface and sufficient numbers of the protein excluding non-adsorbing groups are exposed to the aqueous environment. Some improvement can be obtained in this way but really it is very slight. Further such lengths of time are of course impractical particularly for the treatment of teeth. Indeed it is often the case that proper orientation never occurs and thus the e.g. protein is not effectively excluded.

According to the present invention there is provided a method of treating a surface to render the surface resistant to undesired adsorption from an aqueous environment which method comprises contacting the surface with a solution containing a polymer mixture comprising
(1) a water-soluble polymer containing (a) reactive groups capable of bonding with the surface to be treated, and (b) hydrophobic groups; and
(2) a water-soluble polymer comprising (c) at least one hydrophilic polymeric chain, and (d) at least one hydrophobic group,
in the presence of water.

According to the present invention there is also provided a composition for treating a surface to render the surface resistant to undesired absorption from an aqueous environment which composition comprises in solution a polymer mixture comprising
(1) a water-soluble polymer containing (a) reactive groups capable of bonding with a surface, and (b) hydrophobic groups; and
(2) a water-soluble polymer comprising (c) at least one hydrophilic, polymeric chain, and (d) at least one hydrophobic group,
in the presence of water.

Surfaces treated according to the present invention are rendered not susceptible in aqueous environments to formation of the said first adsorbed layer and accordingly are not susceptible to colonisation by micro-organisms. To the extent that any protein and/or muco-polysaccharide may be adsorbed on the surface this will be in such reduced concentration that very few sites indeed become available for colonisation by the micro-organism.

The surfaces which can be treated according to the invention to render them less susceptible to colonisation by micro-organisms can be very diverse in character. Thus one practical application of the present invention is in the protection of teeth against colonisation, and therefore also attack, by bacteria. The present invention may also be used to prevent or reduce the fouling by micro-organisms of floating or submerged structures such as the hulls of ships, and marine structures. The present invention may also be used to prevent or reduce the accumulation of contamination of equipment or apparatus which inevitably occurs during many both large and small scale industrial processes, e.g. in cooling towers, heat exchangers, food processing plant, and medical treatment processes.

The present invention can also be used to provide surfaces which are not susceptible to e.g. protein adsorption and accordingly to reduce protein losses from aqueous systems where such losses are undesired. Thus, for example, losses due to adsorption on to apparatus walls during protein preparations can be minimised.

In particular the present invention provides an aqueous composition comprising, in solution, a polymer as defined above under (1) and a polymer as defined above under (2). These aqueous compositions may be applied to surfaces to render those surfaces not susceptible to adsorption of proteins or mucopolysaccharides and accordingly, if appropriate, not susceptible to colonisation by micro-organisms. Moreover with the present invention the aqueous compositions provide protection to surfaces in a very short period of time.

While not wishing to be restricted to any theory, for the assistance of understanding it is believed helpful to give the following explanation of the mechanism by which protection is believed to be afforded. The polymers used according to the present invention adopt on the surface to which they are applied a highly oriented arrangement which leads to the advantages according to the invention. In particular the polymers adopt a laminar structure on the surface with reactive groups (a) of polymer (1) attached to the surface. The hydrophobic groups (b) of polymer (a) and the hydrophobic groups (d) of polymer (2) form a hydrophobic layer over the surface and the hydrophilic chains (c) of polymer (2) extend from this hydrophobic layer. Thus there is formed to the outside of the layer of high concentration of hydrophilic chains (c) and these hydrophilic chains will have a tendency to swell by absorption of water. Thus there is formed a well extended high concentration layer to the exterior of the surface formed from these hydrophilic chains. This high concentration layer provides a layer on the surface protective against a surrounding aqueous environment. For example interaction with polymer molecules in a surrounding aqueous environment in particular interaction with any protein or mucopolysaccharides which may be present is reduced. This prevents the formation e.g. of the first adsorbed layer and accordingly rendering the surface non-susceptible to colonisation by micro-organisms.

The laminar orientation of the polymer mixture according to the invention is the preferred orientation and accordingly this structure is rapidly obtained, especially from aqueous solution. In dilute aqueous solution micelles containing both polymers will form. The reactive groups (a) of polymer (1) and the hydrophilic chains (c) of polymer (2) will tend to position themselves on the outside of the micelle while the hydrophobic groups (b) of polymer (1) and the hydrophobic groups (d) of polymer (2), which tend to be rejected by the water molecules, form the inner micelle wall. When such a solution is applied to a surface to be treated, the reactive groups (a) of polymer (1) attach themselves to the surface and the micelle rearranges to give greater phase separation between the reactive groups (a) and the hydrophilic chains (c) of polymer (2). Thus the micelle formation changes to a lamina formation with the hydrophilic chains (c) to the exterior and the reactive groups (a) adjacent to the surface and the hydrophobic groups (b) and (d) of the two polymers therebetween. It is this laminar structure, arising from the nature of the interaction of the polymers (1) and (2), which is believed to give rise to the protective behaviour obtained according to the present invention. When the polymers are applied in solution, as they are already aligned in the micelle in the solution they go to this laminar formation very quickly.

Figure 2:
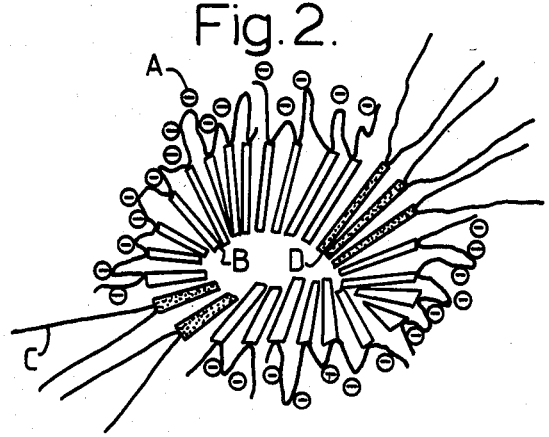
Figure 3:
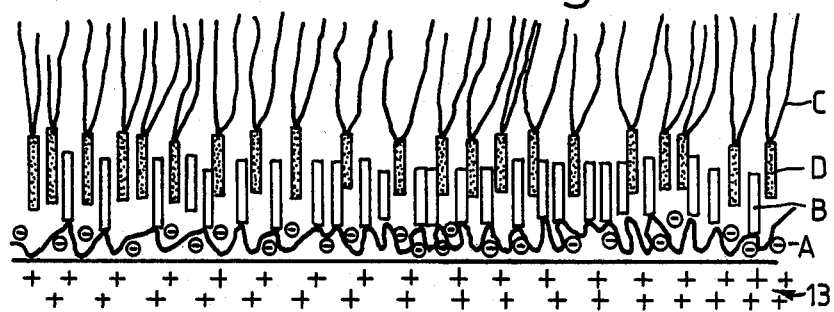

This mechanism is illustrated diagrammatically in FIGS. 1 to 3 of the accompanying drawings.

In FIG. 1 is represented a random copolymer 11 comprising reactive groups A, which are chelating groups with an effective negative charge, and groups with hydrophobic pendant chains B and a star copolymer 12 comprising hydrophilic branches C and a hydrophobic group D.

In FIG. 2 is shown a micelle formed in aqueous solution with the chelating groups A and hydrophilic branches C on the outside of the micelle and with the hydrophobic groups B and D of the two polymers to the inside of the micelle.

FIG. 3 then shows the orientation of the polymers obtained after treatment of a surface 13 having a positive potential with the treatment solution. As can be seen the micelles rearrange themselves to a laminar type formation. The chelating groups A bond to the surface treated. The hydrophobic groups B of the polymer 11 and the hydrophobic branch D of polymer 12 align themselves in a layer with the hydrophilic branches C, which tend to absorb water, being exposed to the outside of the laminar formation. In this way there is built up on the surface a well extended high concentration of hydrophilic groups which will reduce interaction with other polymer molecules.

In more concentrated aqueous solutions the polymer mixture according to the present invention may adopt a laminar rather than a micelle conformation but as will be seen in this also the polymers will already be aligned within the solution and thus again the length of time taken to form an aligned polymer system on the surface treated is minimised.

It is thus interaction between component parts of the two polymers essential to the composition according to the present invention which ensures their correct alignment, in particular in solution, resulting in the required protection.

Suitable individual polymers for use according to the invention can be readily prepared and at relatively low cost. Indeed in some cases the polymers used are commercially available.

The polymers (1) used according to the present invention contain (a) reactive groups capable of bonding with a surface and (b) hydrophobic groups. These polymers (1) can be random, graft, block or star copolymers. If appropriate these polymers (1) may be derived from a homo- or co-polymer on to the chain of which are introduced, as appropriate, reactive groups and/or hydrophobic groups. Preferably however the polymer (1) is a random copolymer derived from a monomer containing the reactive group and a hydrophobic group-containing comonomer.

The reactive groups (a) will be chosen according to the surface to be treated. The bonding to the surface can be of an ionic nature in which case the effective charge of the reactive group will be opposite to that of the surface. Preferably the bonding is by removal of an ion from the surface treated but it may also be the result of salt formation. In the case of for example the treatment of teeth, the nature of the ionic bonding may not be important since the tooth surface can act amphoterically with either calcium or phosphate ions being removed. Alternatively the bonding may be of a covalent nature for example with the reactive group being capable of substitution into the lattice of the substrate. Preferably the reactive groups are groups capable of chelation. Suitable reactive groups include carboxylates, phosphates, sulphates, phosphonates, amines, quaternary ammonium, silanes, salts or acids, polyimines. Thus comonomers used in the preparation of polymer (1) can for example be an organic acid or base, a quaternarised base or a coupling agent.

Generally speaking for the treatment of teeth the reactive grups (a) of polymer (1) are suitably carboxylic acid or salt groups. Carboxylic acid or salt groups are also suitable for use in the treatment of mild steel. For the treatment of stainless steel surfaces the reactive groups (a) are preferably phosphates to obtain sufficient bonding to the surface. Sulphate reactive groups may be used in the treatment of special steel and light alloy surfaces and silane reactive groups may be used in the treatment of glass and porcelain.

The hydrophobic comonomers used in the preparation of polymer (1) may be any suitable organic hydrophobic group-containing comonomer. The hydrophobic groups are preferably derived from monomers containing a chain of between 7 and 20 carbon atoms. Most suitably the chain is a saturated alkyl chain containing 7 to 20 carbon atoms but in addition aromatic, substituted aromatic and cycloaliphatic groups can be used as can unsaturated aliphatic chains. Suitably the comonomer used is a hydroxy-substituted alkane, a halogenated alkane or an unsaturated hydrocarbon. Preferably though there is used here a long chain ($C_7$–$C_{20}$, most preferably $C_{13}$) alkyl ester of methacrylic acid. Generally speaking the carbon atom content of the hydrophobic group must not be so great that the polymer is water insoluble and not be so small that the group does orientate according to the invention. Such groups and comonomers are also suitable for use as the hydrophobic portions (d) of polymer (2).

It has been found, particularly in the treatment of teeth, a preferred copolymer (1) having carboxylic acid reactive groups (a) is a random copolymer of acrylic acid and $C_{13}$ n-alkyl ester of methacrylic acid. Suitably the copolymer contains 20 to 37% by weight of the $C_{13}$ n-alkyl ester. At higher $C_{13}$ n-alkyl ester contents the copolymer becomes incapable of entering into solution in water. Most efficient expelling of protein from the surface is achieved with a 33% ester content though even a copolymer with a 10% ester content is capable of exhibiting protein exclusion.

Suitable phosphate-containing polymers (1) may be obtained by copolymerising e.g. poly(diethyl vinyl phosphonate) and the $C_{13}$ n-alkyl ester of methacrylic acid and subsequently oxidising the phosphonate groups of polymer obtained, e.g. using nitrous oxide. However this is a difficult and somewhat expensive process to carry out. Alternatively the hydroxy groups on copolymers containing a hydroxyalkyl methacrylate (preferably hydroxy-ethyl- or -propyl-methacrylate) and a long chain alkyl ester of methacrylic acid (and optionally also acrylic acid which has been found useful to reduce the molecular weight of the final polymer and to facilitate phosphation) can be converted into phosphate groups by reaction with phosphoric acid in the presence of urea or phosphorus pentoxide.

Suitable sulphate-containing polymers (1) may be obtained by introduction of sulphate groups into suitable styrene-containing copolymers e.g. styrene/$C_{13}$ alkyl methacrylic acid ester random copolymer or by polymerisation of the reaction product of methacroyl chloride and sulphanilic acid, with a long chain alkyl ester of methacrylic acid, especially $C_{13}$ n-alkyl ester.

Other suitable copolymers (1) include vinyl benzyl phosphonate/$C_{13}$ n-alkyl ester of methacrylic acid, and quaternarised random copolymer of 4-vinyl pyridine and $C_{13}$ n-alkyl ester of methacrylic acid.

The polymer (2) is suitably a block, graft or star copolymer. In addition to the hydrophobic group (d), this copolymer contains a hydrophilic chain which provides the exterior layer of the treated surface. It is this chain which gives rise to the protein or mucopolysaccharide non-adsorbing properties of the surface treated according to the present invention. Such groupings are suitably derived from hydroxy-substituted methacrylates, polyethylene oxides, polyethers, polyvinyl-pyrrolidone, polyvinyl alcohol, poly-acrylamides and polysaccharides.

Particularly suitable for use as polymer (2) according to the invention are the polyoxyethylene derivatives of fatty acid partial esters of sorbitol anhydride such as are sold under the trade mark TWEEN.

To ensure water solubility, the molecular weights of th polymers need to be controlled. This can be achieved by using e.g. chain transfer agents in the preparation of polymer (1). Generally the molecular weight of polymer (1) will be less than 300,000.

Suitably polymers (1) and (2) are present in the solution used according to the present invention in amouns such that there is at least an equimolar quantity of hydrophobic groups (d) of polymer (2) as of hydrophobic groups (b) of polymer (1). Preferably in the polymer mixture there are present substantially equimolar amounts of hydrophobic groups (b) and hydrophobic groups (d). The reason for this is believed to be that at the 50:50 ratio of hydrophobic groups (b) and (d) substantially all the available sites for polymer (2) on the surface being treated are taken up. If there is less than 50% of hydrophobic groups (d), some of the surface sites will be unoccupied. If there is more than 50% of hydrophobic groups (d), there may be some occupancy of sites by site sharing for example, but in the main polymer (2) will be in excess and for example will be lost in solution. Generally speaking the molar ratio of hydrophobic groups (b) to hydrophobic groups (d) should be between 1:0.9 and 1:1.5, with the ratio 1:1 being preferred.

The method of application of the polymer combination according to the present invention will depend upon the kind of surface being treated. For the treatment of teeth, the polymers may be used in the form of a mouthwash. For, for example, surfaces in apparatus or equipment it may be appropriate to rinse the apparatus or equipment with water to which the polymers have been added. Thus the polymer mixture according to the invention forms substantially a protective monolayer on the treated surface. Thus there is obtained the protection according to the invention without any substantial loss of efficiency in the case of apparatus such as heat exchangers.

Although for rapid application the polymer mixture according to the invention is applied from aqueous solution, in other applications while naturally it is important that the correct formation is obtained on the final treated surface, the speed of attaining the structure may not be so important. In these cases the polymer mixture may for example be applied as a paint, e.g. sprayed, in which paint the polymer mixture, in the presence of water which will hydrate the hydrophilic groups, is contained in a volatile solvent e.g. ethyl alcohol. After evaporation of the solvent, there is deposited on the surface a protective polymer layer in accordance with the invention. Such paints can be used in the treatment of ship's hulls or marine structures to prevent the build up of fouling bacteria and to paint the inside of heat exchangers. In both cases it may be desirable to apply several polymer-containing paint layers.

In aqueous solution the polymer mixture according to the present invention may flocculate due to the formation of hydrogen bonds and interaction between the reactive groups (a) of polymer (1) and polymer (2). Use of such solutions can lead to the formation of unorientated polymer layers on the surface being treated. It is then preferred to add to the solution a compound which is capable of weakening or preventing the formation of hydrogen bonds and thus breaks down the complexes formed in solution. Generally the more reactive groups (a) present in polymer (1), the more such compound is required. A preferred group of such compounds are the proton acceptors, and examples of suitable proton acceptors include alcohols, for example methyl alcohol, ethyl alcohol, propan-2-ol and t-butyl alcohol, ketones, for example acetone, butan-2-one and acetyl acetone, glycols for example ethylene glycol, ureas for example urea and thiourea, and amines for example ethanolamine. Particularly good results have been obtained using ethyl alcohol. There may also be used compounds containing chaotropic or structure breaking ions such as, for example, the perchlorate ion and the hexametaphosphate ion e.g. sodium hexametaphosphate.

Aqueous compositions according to the present invention may be used to prevent bacterial attack on teeth by preventing colonisation of teeth by bacteria which in turn is prevented by preventing or mitigating the build up of protein on the surface of the teeth. This can simply be achieved by using an aqueous composition according to the present invention as a mouthwash. The patient merely has to carry out a daily mouthwash to prevent the build up of plaque on the teeth.

Such treatment compositions must of course be physiologically acceptable and will generally contain water and alcohol in addition to the polymer mixture which will normally be present in amounts of 5 to 10% by weight. The two polymers may be mixed with water to form a suspension and then the suspension clarified by addition of ethyl alcohol.

Other applications in which micro-organism colonisation can be a problem and accordingly which can benefit from treatment using the aqueous composition according to the present invention include for example medical apparatus particularly kidney machines and artificial veins and organs which can be treated with the composition to render them able to work longer before contamination. Similarly the present compositions can be used to reduce e.g. protein losses in apparatus by reducing the tendency of the apparatus to adsorb protein. Also domestically the aqueous compositions could for example be used in the treatment of toilet bowls to prevent micro-organism build up. In each case the article to be protected can be contacted e.g. by simple rinsing with an aqueous composition according to the invention.

With the aqueous compositions of the present invention, the pre-alignment of polymer molecules within the composition prior to application means the length of time which such compositions have to be in contact with the surface being treated can be very small e.g. a matter of milliseconds in the case of the very dilute compositions used as mouthwashes. In this way there is very quickly and easily obtained good protection against bacterial decay of teeth.

For applications such as the prevention of micro-organism colonisation in toilet bowls stronger solutions e.g. up to about 30% by weight may be suitable for adding to the cistern water.

In some applications particularly with paints it may be desirable to strengthen and decrease the solubility of the final coating by cross-linking between the hydrophobic groups of polymer (1) and those of polymer (2) in situ. This can be done by using cross-linkable groups in the hydrophobic groups (b) and (d) of the two polymers. For example there may be used unsaturated hydrocarbons groups e.g. diacetylene, allyl, butadiene or by incorporating groupings susceptible to ring opening reactions. The cross-linking can be effected e.g. by the use of electron beams, by exposure to U.V. or visible light or by condensation. If the two hydrocarbon groups are themselves reactive with each other then the polymers should only be mixed just prior to coating. Alternatively if a free radical polymerisation reaction is used peroxides, hydroperoxides or azo-type catalysts can be incorporated into the mixture or the cross-linking can be promoted by exposure to tertiary amine solution or vapour. Although the ingredients of the coating composition may not be in such cases immediately reactive the coating compositions still tend to have short shelf lives and thus mixing of the ingredients just prior to application of the coating is still desirable. Drying oils may be incorporated into paint compositions according to the invention.

Figure 4:
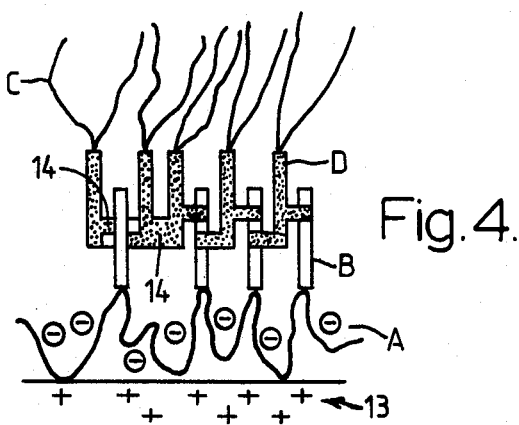

FIG. 4 of the accompanying drawings shows diagrammatically the structure of a coating obtained in accordance with FIGS. 1 to 3 in which the hydrophobic groups of the two polymers are joined by cross-links 14.

To illustrate the properties of the compositions according to the present invention, columns of hydroxy apatite were prepared. These columns were treated with a test solution and then a solution of protein was passed through the column and the effluent analysed to determine the percentage of protein eluted from the column.

The polymer mixture used contained, as polymer (1), a random copolymer prepared from acrylic acid and $C_{13}$ alkyl methacrylic acid and $C_{13}$ alkyl methacrylic acid ester thus having units of the formulae:

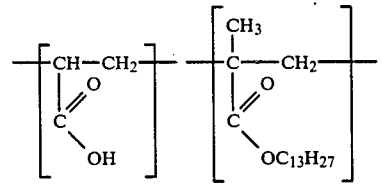

The weight ratio of acrylic acid monomer to $C_{13}$ alkyl methacrylic acid ester used in the preparation of the copolymer was varied from 25% by weight through 20% to 16% by weight $C_{13}$ alkyl methacrylic acid ester.

As polymer (2) there was used a copolymer consisting of a polyoxyethylene chain attached, via a sorbitol group, to a mono-oleate alkyl chain (Tween 80 ex Atlas Chemical Industries Limited).

A treatment solution was made up as a 50/50 volume by volume mixture of a 0.5% by weight solution of random copolymer in water and a 1.5% by weight solution of Tween 80. A volume of this treatment solution was then passed through the hydroxy apatite column. The column was then treated with 2 ml of bovine serum albumin solution in pH 7 phosphate buffer (50 mg/ml). The content of bovine serum albumin in the effluent was then determined using a U.V. spectrometer.

Figure 5:
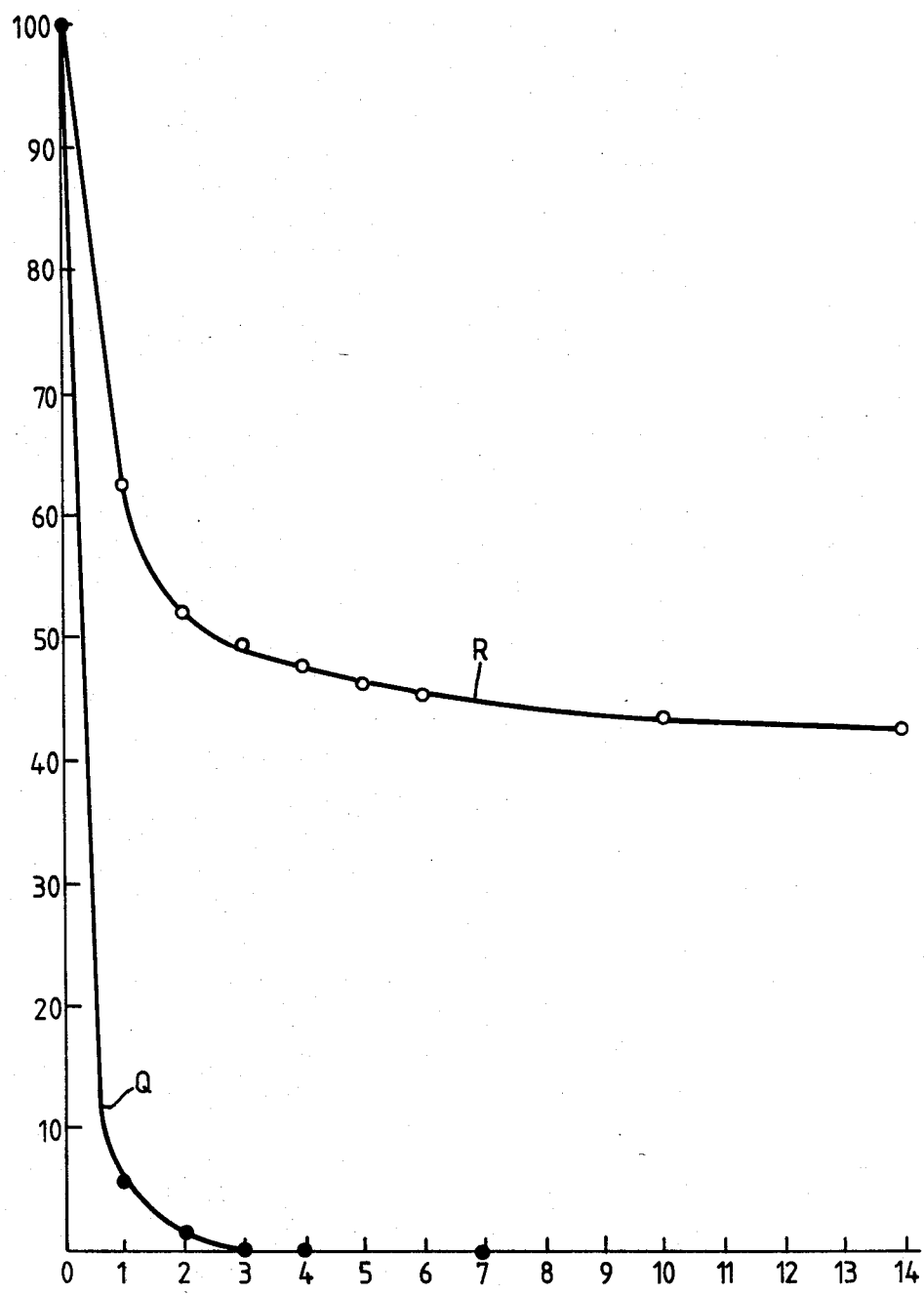
Figure 6:
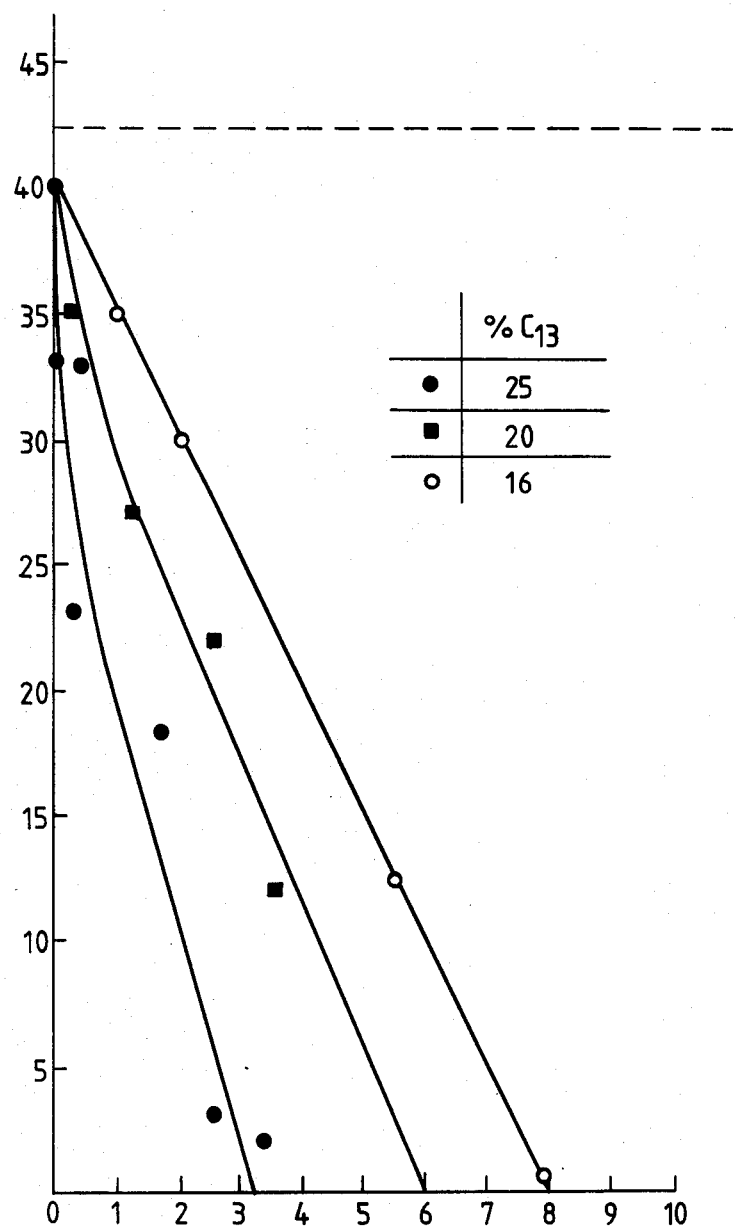

The results are shown in FIGS. 5 and 6 of the accompanying drawings.

FIG. 5 compares the effect of the surface treatment on protein adsorption when 10 ml of the treatment solution containing a random polymer containing 25% by weight of the $C_{13}$ alkyl methacrylic acid ester was used (Curve Q) as compared with the case when no prior treatment was carried out (Curve R). The ordinate records the percentage of protein eluted and the abscissa the fractions (3 ml). As can be seen, whereas with no prior treatment the minimum percentage of uneluted protein exceeded 40%, with the treatment according to the present invention substantially 100% of the protein was uneluted i.e. unadsorbed after the third fraction.

FIG. 6 compares the protein adsorption of polymer mixtures containing, as random copolymers, copolymers derived from respectively 25%, 20% and 16% by weight $C_{13}$ alkyl methacrylic acid ester using various volumes of treatment solution on protein adsorption using a 15 cm hydroxyapatite column. The ordinate records the percentage of protein adsorbed and the abscissa the volume of treatment solution (ml) used. There is shown in dotted line the percentage of protein adsorbed on an untreated column.

It can be seen from FIG. 6 that as the volume of treatment solution is reduced so the volume of protein unadsorbed is also reduced. Moreover the use of increasing amounts of the hydrophobic $C_{13}$ alkyl methacrylic acid comonomer in the random copolymer results in decreased protein adsorption. It is believed that the reason for this is that the effect of reducing the hydrophobic content of the first polymer (1) results in a corresponding reduction in the bonding of the polymer (2) thereto and accordingly results in a reduction in the effective hydrophilic group concentration on the surface of the treated hydroxy apatite.

This invention is further illustrated in the following Examples wherein Examples 1 to 6 relate to the preparation of polymer suitable for use as polymer (1) in the present mixtures and Example 7 relates to aqueous composition suitable for use as mouthwashes. The $C_{12.5}$ alkyl methacrylic acid esters referred to in some of the Examples were fractions of such esters having an average carbon atom content of 12.5 and comprising mainly the $C_{13}$ alkyl ester but also some $C_{12}$ and $C_{11}$.

EXAMPLE 1

Preparation of random copolymer of acrylic acid and $C_{13}$ alkyl methacrylic acid ester containing 25% ester.

180 g water and 1.2 g ammonium persulphate were introduced into a 500 ml flanged flask fitted with an $N_2$ inlet, a dropping funnel, a reflux condenser and a stirrer. The flask was degassed with $N_2$ for one hour in an oil bath at 80°–85° C.

40 g of distilled acrylic acid and 20 g of $C_{13}$ alkyl methacrylic acid ester (previously washed with 0.1N NaOH to remove inhibitor) were introduced into the dropping funnel and added into the flask over four hours. The temperature was raised to 100°–110° C. for one hour.

Excess water was distilled off under vacuum and the product precipitated in acetone and dried under vacuum.

EXAMPLE 2

Preparation of quaternarised random copolymer of 4-vinylpyridine and $C_{13}$ alkyl methacrylic acid ester.

Using apparatus the same as that used in Example 1, 190 g ethanol, 8 g water and 2 g azoisobutyronitrile were introduced into the flask which was heated to 60° C. in a water bath and flushed with $N_2$. 41.5 g 4-vinylpyridine and 20 g $C_{13}$ alkyl methacrylic acid ester were added dropwise to the flask with stirring from the dropping funnel. The stirring was continued for 20 hours and then the polymer was precipitated in diethyl ether and dried in vacuum.

50 ml TMSO (tetramethylene sulphone), 10.5 g of the polyvinyl pyridine copolymer and 6 g hexadecyl bromide were introduced into a three necked flask equipped with a stirrer, dropping funnel and reflux condenser and heated in an oil bath to 50° C. for three days. Then 22 g ethyl bromide were added and the mixture refluxed at 45° C. for three days. The product obtained was precipitated in acetone, filtered and dried under vacuum.

In the product obtained in this way, some of the quaternarised vinyl pyridine groups bear hydrophobic hexadecyl chains while others are quaternarised by the ethyl bromide to give rise to reactive groups according to the present invention.

In a similar manner a polymer suitable for use as polymer (1) in accordance with the present invention can be prepared from polyvinyl pyridine homopolymer since the quaternarisation will be substantially random. Thus some of the quaternarised groups will bear the hydrophobic hexadecyl groups while others will be quaternarised by the reactive ethyl bromide-derived groups.

EXAMPLE 3

Preparation of random copolymer of vinyl benzyl phosphonate and $C_{13}$ alkyl methacrylic acid ester.

Vinyl benzene phosphonate was prepared by chloromethylating benzene by the procedure of Kindler, Hansen and Koebk (Ann. Chem. 617, 25, 1958). 1 mole p-(2-chloroethyl)-α-chlorotoluene was heated to 140°–155° C. under $N_2$ and 95 ml triethyl phosphite was added. The mixture was heated for one hour and then diethyl-p-(2-chloroethyl)-benzyl phosphonate was distilled off at 140°–150° C./0.2 torr. The ethyl ester was hydrolysed for two hours using a 2:3 v/v mixture of 48% HBr and formic acid. The product was dehydrochlorinated using potassium ethoxide followed by acidification with HCl. The monomer was then flash distilled using $10^{-5}$ torr vacuum at room temperature.

The vinyl benzyl phosphonate/$C_{13}$ alkyl methacrylic acid ester copolymer was then prepared in analogous manner to the 4-vinyl-pyridine copolymer of Example 2 with the phosphonate being used in the form of its sodium salt.

Similar polymers but having unsaturated side chains can be prepared by preparing a homopolymer of vinyl benzyl phosphonate and condensing this homopolymer with the diacetylene-substituted acid chloride described in Example 4 below or by replacing some of the $C_{13}$ alkyl methacrylic acid ester used in the preparation of the copolymer by methacroyl chloride with subsequent reaction with allyl alcohol in the presence of pyridine at 50° C.

EXAMPLE 4

Preparation of random copolymer of sulphonated styrene and $C_{13}$ alkyl methacrylic acid ester.

A random copolymer of styrene and $C_{13}$ alkyl methacrylic acid ester was prepared by emulsion polymerisation as follows: There were introduced into a flanged flask having a stirrer, reflux condenser and $N_2$ inlet 200 g degassed water, 2 g gelatine, 40 g styrene (redistilled), 20 g $C_{13}$ alkyl methacrylic acid ester, 0.3 g benzoyl peroxide. The mixture was heated to 80° C. for 24 hours and the beads obtained washed with enzyme detergent and then with cold water.

The styrene groups were sulphonated by the use of a 3:1 $SO_3/(EtO)_3.P=O$ complex by the methods of Taback (Ind. Eng. Chem. Prod. Res. Dev. 1 (4), 275, 1962) and Nashay and Reberson (J. Appl. Pol. Sci. 20, 1885, 1976). The complex was prepared in a three necked flask equipped with a stirrer, dry nitrogen inlet and dropping funnel. 0.038 ml triethyl phosphite in 20 ml dichloroethane were introduced into the flask and then 4.8 ml distilled $SO_3$ were added dropwise at 0° C. and then the mixture allowed to come to room temperature.

Into a similar apparatus there was introduced a 2% solution of the polymer in dichloroethane and the complex was added in an equimolar amount based on the styrene content of the polymer. The mixture was hydrolysed to sulphonate the styrene groups for two hours using 0.25M NaOH.

Unsaturated groups can be introduced into the polymer for the purposes of cross-linking by the method of Hub, Hupfer, Koch, and Ringsdorf (Colloid Pol. Sci. 255, 521, 1977) to give diacetylenic cross-linking groups or, using methacroyl chloride, methacrylate groups. The diacetylene was prepared using the method of Chodkievicz (Ann. Chem. (Paris) 2, 852, 1957) according to the reaction:

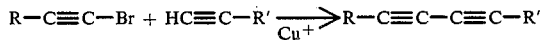

The bromoacetylene was prepared by the method of Strauss et al (Ber, 63B, 1868, 1930) by the action of the hypobromic acid on an acetylene. The diacetylene is acylated by alcohol, alcohol amine, sulphonic acid after conversion to the acid chloride. Thus, if R' is a fatty acid group, the diacetylene is converted to the acid chloride using oxalylchloride and can be acylated at 0° C. in dry chloroform in the presence of pyridine.

EXAMPLE 5

Preparation of random copolymer of the reaction product of methacroyl chloride and sulphanilic acid and $C_{12.5}$ alkyl methacrylic acid ester.

Sulphanilic acid, crushed in pestle and mortar (17 g), was stirred with heating overnight in water (approximately 800 ml). The solution was cooled to 5° C. and methacroyl chloride (5 g) was added dropwise with stirring. The reactants were then stirred for a few days. An orange brown solution formed which was then filtered. Excess water was removed on a rotary evaporator. On cooling overnight, white crystals formed which were filtered off, washed with alcohol and dried under vacuum to give a white powder.

The white powder (3 g) and $C_{12.5}$ alkyl methacrylic acid ester (9 g) was stirred under nitrogen with azoisobutyronitrile (0.005 g) and dodecyl mercaptan (0.02 g) and heated to 60° C. for two hours.

EXAMPLE 6

Preparation of phosphated acrylic acid/hydroxyethyl methacrylate/$C_{12.5}$ alkyl methacrylic acid ester copolymer.

Hydroxyethyl methacrylate (10 g), redistilled acrylic acid (20 g) and inhibitor free $C_{12.5}$ alkyl methacrylic acid ester (30 g) were added dropwise, over two hours, with stirring, to distilled water (180 g) and ammonium persulphate (1.2 g) at 80°–85° C. and flushed with nitrogen. The reaction mixture was then heated to 100°–110° C. for another hour. A thick white emulsion was formed.

The emulsion (100 ml) was added to 85% $H_3PO_4$ (45 g) and urea (27 g), warmed to 60° C. The mixture was stirred to give a homogeneous emulsion and gradually heated to 100° C. with stirring. The mixture was then heated to 105° C. in an oven to drive off water and then to 150° C. to decompose the urea. The mixture bubbled and foamed and expanded.

The resulting solid was then acidified with hot hydrochloric acid (2N), precipitated in acetone, redissolved in water and passed through an $H^+$ ion exchange column.

EXAMPLE 7

Typical treatment solutions in particular for the treatment of teeth were prepared as follows (percentages are by weight):

5 ml of a 5% solution in water of random copolymer comprising 75% acrylic acid units and 25% $C_{12.5}$ alkyl methacrylic acid ester by weight were added to 5 ml of a 15% solution of Tween 80 (ex Atlas Chemical Industries Limited) in water with stirring. 10 ml ethyl alcohol were then added to the suspension formed, which clarified.

5 ml of a 5% solution in water of random copolymer comprising 80% acrylic acid units and 20% $C_{12.5}$ alkyl methacrylic acid ester by weight were added to 5 ml of a 15% solution of Tween 80 (ex Atlas Chemical Industries Limited) in water with stirring. 10 ml ethyl alcohol were then added to the suspension formed, which clarified.

5 ml of a 5% solution in water of random copolymer comprising 84% acrylic acid units and 16% $C_{12.5}$ alkyl methacrylic acid ester by weight were added to 5 ml of a 15% solution of Tween 80 (ex Atlas Chemical Industries Limited) in water with stirring. 15 ml ethyl alcohol were then added to the suspension formed, which clarified.

I claim:

1. A method of treating a surface to render the surface resistant to undesired adsorption from an aqueous environment, which method comprises contacting the surface with a solution containing a polymer mixture comprising
   (1) a water-soluble polymer comprising a polymer backbone having thereon (a) reactive groups capable of bonding with the surface to be treated, and (b) hydrophobic groups each containing 7 to 20 carbon atoms; and
   (2) a water-soluble polymer comprising (c) at least one hydrophilic polymeric chain and (d) at least one hydrophobic group containing 7 to 20 carbon atoms; the molar ratio of hydrophobic groups (b)

of polymer (1) to hydrophobic groups (d) of polymer (2) being between 1:0.9 and 1:1.5 and a proton acceptor capable of reducing or preventing hydrogen bond formation, in the presence of water.

2. A method according to claim 1, wherein polymers (1) and (2) are in solution in water when contacted with the surface.

3. A method according to claim 1, wherein the polymers (1) and (2) in solution in a volatile solvent are applied to the surface and the volatile solvent is allowed to evaporate.

4. A method according to claim 3, wherein the hydrophobic groups (b) of polymer (1) and the hydrophobic groups (d) of polymer (2) are caused to crosslink after application.

5. A method according to any one of claims 1 to 4, wherein the surface is of mild steel and the reactive groups (a) of polymer (1) are carboxylic acid or carboxylic acid salt groups.

6. A method according to claim 5, wherein polymer (1) is a copolymer of acrylic acid and a $C_7$ to $C_{20}$ n-alkyl ester of methacrylic acid.

7. A method according to any one of claims 1 to 4, wherein the surface is of stainless steel and the reactive groups (a) of polymer (1) are phosphate acid or salt groups.

8. A method according to any one of claims 1 to 4, wherein polymer (2) is a polyoxyethylene derivative of a fatty acid partial ester of sorbitol anhydride.

9. A method of treating teeth to render the teeth resistant to bacterial colonization, which method comprises contacting the teeth with an aqueous mouthwash containing, in solution, a polymer mixture comprising (1) a water-soluble polymer comprising a polymer backbone having thereon (a) reactive groups capable of bonding to the surface of teeth and (b) hydrophobic groups each containing 7 to 20 carbon atoms; and (2) a water-soluble polymer comprising (c) at least one hydrophilic polymeric chain and (d) at least one hydrophobic group containing 7 to 20 carbon atoms; the molar ratio of hydrophobic groups (b) of polymer (1) to hydrophobic groups (d) of polymer (2) being between 1:0.9 and 1:1.5 and a proton acceptor capable of reducing or preventing hydrogen bond formation.

10. A method according to claim 9, wherein the reactive groups (a) of polymer (1) are carboxylic acid or carboxylic acid salt groups.

11. A method according to claim 9 or 10, wherein polymer (1) is a copolymer of acrylic acid and a $C_7$ to $C_{20}$ n-alkyl ester of methacrylic acid.

12. A method according to claim 11, wherein polymer (1) is a copolymer of acrylic acid and $C_{13}$ n-alkyl ester of methacrylic acid containing 20-37% by weight of the ester.

13. A method according to claim 9, wherein polymer (2) is a polyoxyethylene derivative of a fatty acid partial ester of sorbitol anhydride.

14. A method according to claim 9, wherein the polymer mixture contains substantially equimolar amounts of hydrophobic groups (b) of polymer (1) and hydrophobic groups (d) of polymer (2).

15. A composition for use in the treatment of surfaces, which comprises, in solution, a polymer mixture comprising (1) a water-soluble polymer comprising a polymer backbone having thereon (a) reactive groups capable of bonding with a surface, and (b) hydrophobic groups each containing 7 to 20 carbon atoms; and (2) a water-soluble polymer comprising (c) at least one hydrophilic polymeric chain and (d) at least one hydrophobic group containing 7 to 20 carbon atoms; the molar ratio of hydrophobic groups (b) of polymer (1) to hydrophobic groups (d) of polymer (2) being between 1:0.9 and 1:1.5 and a proton acceptor capable of reducing or preventing hydrogen bond formation, in the presence of water.

16. A composition according to claim 15, wherein polymers (1) and (2) are in solution in water.

17. A composition according to claim 15, wherein it is in the form of a paint comprising polymers (1) and (2) in solution in a volatile solvent.

18. A composition according to claim 17, wherein the hydrophobic groups (b) of polymer (1) and the hydrohobic groups (d) of polymer (2) are crosslinkable.

19. A composition according to any one of claims 15 to 18, wherein the reactive groups (a) of polymer (1) are carboxylic acid or carboxylic acid salt groups.

20. A composition according to claim 19, wherein polymer (1) is a copolymer of acrylic acid and a $C_7$ to $C_{20}$ n-alkyl ester of methacrylic acid.

21. A composition according to any one of claims 15 to 18, wherein the reactive groups of polymer (1) are phosphate acid or salt groups.

22. A composition according to any one of claims 15 to 21 characterised in that polymer (2) is a polyoxyethylene derivative of a fatty acid partial ester of sorbitol anhydride.

23. An aqueous composition which is a mouthwash, which comprises, in aqueous solution, a polymer mixture comprising (1) a water-soluble polymer comprising a polymer backbone having thereon (a) reactive groups capable of bonding to the surface of teeth and (b) hydrophobic groups each containing 7 to 20 carbon atoms; and (2) a water-soluble polymer comprising (c) at least one hydrophilic polymeric chain and (d) at least one hydrophobic group containing 7 to 20 carbon atoms; the molar ratio of hydrophobic groups (b) of polymer (1) to hydrophobic groups (d) of polymer (2) being between 1:0.9 and 1:1.5 and a proton acceptor capable of reducing or preventing hydrogen bond formation.

24. A composition according to any one of claims 15 or 23, wherein the polymer mixture contains substantially equimolar amounts of hydrophobic groups (b) of polymer (1) and hydrophobic groups (d) of polymer (2).

25. The method of any of claims 1, 9, 15 or 23, wherein said hydrophobic groups (b) are derived from monomers containing a chain of between 7 and 20 carbon atoms.

26. The method of any of claims 1, 9, 15 or 23, wherein said hydrophobic groups (d) are derived from monomers containing a chain of between 7 and 20 carbon atoms.

27. A composition for use in the treatment of surface, which comprises a polymer mixture comprising (1) a water-soluble polymer comprising a polymer backbone having thereon (a) reactive groups capable of with the surface to be treated, and (b) hydrophobic groups, the reactive groups (a) and hydrophobic groups (b) being attached to different atoms of the backbone;

(2) a water-soluble polymer comprising (c) at least one hydrophilic polymer chain and (d) at least one hydrophobic group; the molar molar ratio of hydrophobic groups (b) of polymer (1) to hydrophobic groups (d) of polymer (2) being between 1:0.9 and 1:1.5 and
a proton acceptor capable of reducing or preventing hydrogen bond formation.

28. An aqueous composition, which is a mouthwash and which comprises, in aqueous solution, a polymer mixture comprising
   (1) a water-soluble copolymer of acrylic acid and a $C_7$ to $C_{20}$ n-alkyl ester of methacrylic acid; and
   (2) a water-soluble polyoxyethylene derivative of a fatty acid partial ester of sorbitol anhydride; the copolymer (1) and polymer (2) containing hydrophobic groups in substantially equimolar amounts, and
ethyl alcohol as a proton acceptor capable of reducing or preventing hydrogen bond formation.

* * * * *